(12) United States Patent
Nielsen

(10) Patent No.: US 7,726,302 B1
(45) Date of Patent: Jun. 1, 2010

(54) INHALATOR FOR TREATMENT OF BRONCHIAL DISORDER IN HORSES

(76) Inventor: Helle Funch Nielsen, Lejlighed 79, Vandtarnsvej 7, DK-3460 Birkerod (DK)

( * ) Notice: Subject to any disclaimer, the term of this patent is extended or adjusted under 35 U.S.C. 154(b) by 901 days.

(21) Appl. No.: 10/129,939

(22) PCT Filed: Nov. 15, 2000

(86) PCT No.: PCT/DK00/00633

§ 371 (c)(1),
(2), (4) Date: Sep. 16, 2002

(87) PCT Pub. No.: WO01/35856

PCT Pub. Date: May 25, 2001

(30) Foreign Application Priority Data

Nov. 16, 1999 (DK) .............................. 1999 01644

(51) Int. Cl.
*A61M 11/00* (2006.01)
(52) U.S. Cl. ............................ 128/200.14; 128/203.12; 128/203.29
(58) Field of Classification Search ............ 128/200.14, 128/200.23, 203.12, 203.15, 203.29, 204.11, 128/204.12
See application file for complete search history.

(56) References Cited

U.S. PATENT DOCUMENTS 4,546,768 A * 10/1985 Ferierabend ............ 128/200.16
4,796,614 A * 1/1989 Nowacki et al. ....... 128/200.14
5,012,804 A * 5/1991 Foley et al. ............ 128/200.23
5,385,140 A    1/1995 Smith
5,427,089 A * 6/1995 Kraemer ................ 128/200.23
5,755,221 A    5/1998 Bisgaard
5,954,049 A * 9/1999 Foley et al. ............ 128/203.29
6,951,215 B1  10/2005 Hoffman

FOREIGN PATENT DOCUMENTS

EP    0 444 905 A1   2/1991
EP    0 537 991 A2  10/1992
GB    2 111 838 A   11/1982

* cited by examiner

*Primary Examiner*—Todd E Manahan
*Assistant Examiner*—Michael G Mendoza
(74) *Attorney, Agent, or Firm*—Merchant & Gould P.C.

(57) ABSTRACT

A device for the treatment of bronchial disorders in horses by inhalation therapy comprising an inhalation spacer (1) with a first (5) and a second (10) opening, an activatable drug atomizer (7) which can be connected with the first opening (5) of the inhalation spacer, and connecting means (11, 14) comprising a hopper-shaped part (13) which at the hopper opening has such size as to be able to cover one of the horse's nostrils, and a valve arrangement comprising two one-way valves (16, 18), one of which (16) allows influx of inhalation air from the inhalation spacer into the hopper-shaped part (14) of the connecting means (11, 14), and the other allows outflux of exhalation air from the hopper-shaped part (14) to the surroundings, and where the inhalation spacer (1) has at least one additional opening (8) with an appertaining one-way valve (9) which allows influx of air from the surroundings into the interior (4) of the inhalation spacer (1).

4 Claims, 2 Drawing Sheets

INHALATOR FOR TREATMENT OF BRONCHIAL DISORDER IN HORSES

Figure 1:
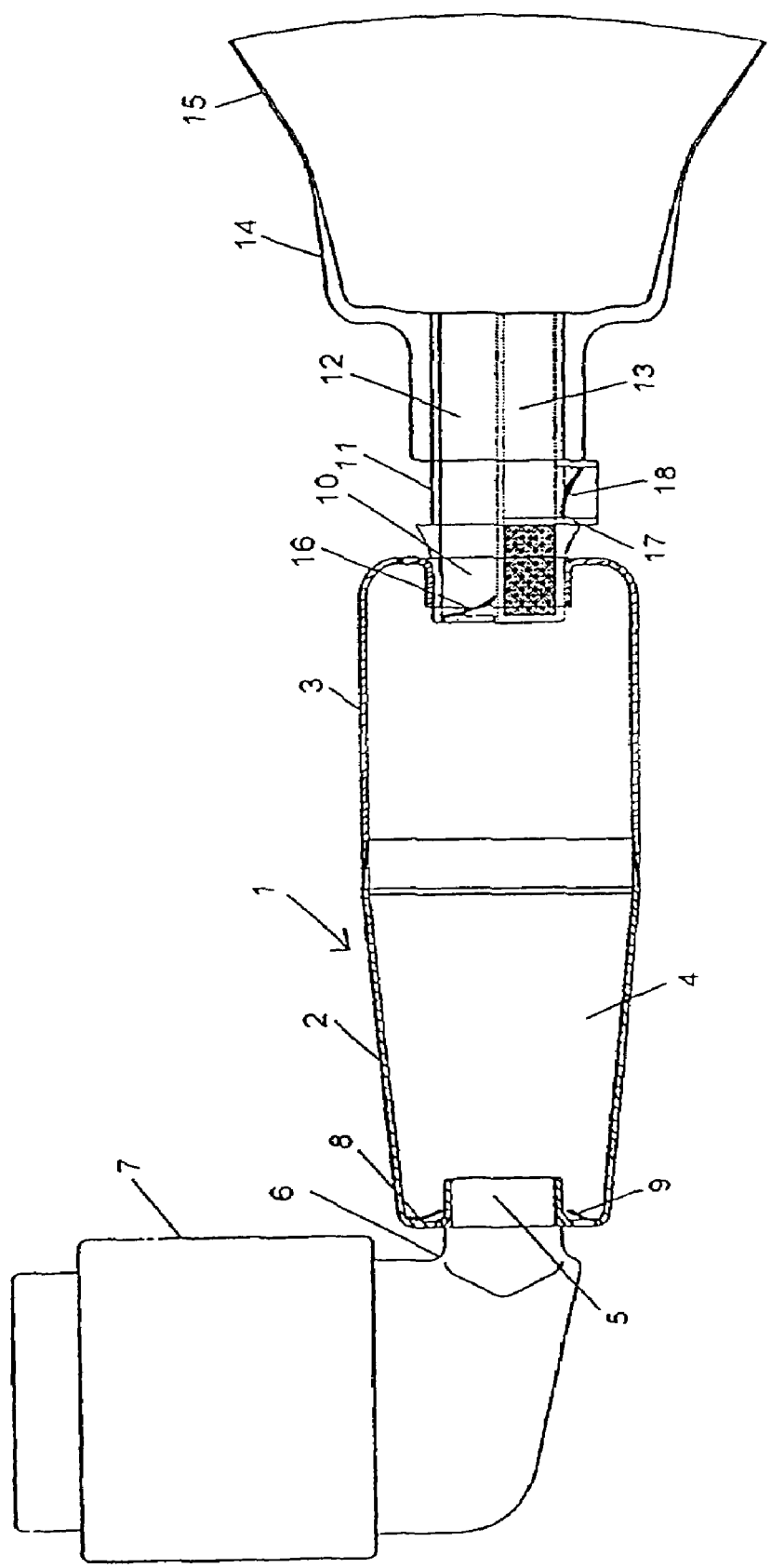

The present invention relates to a device for the treatment of bronchial disorders, and in particular allergic or inflammatory bronchial disorders, in horses by inhalation therapy.

It is well-known that horses, e.g. sports horses, may be afflicted by bronchial disorders which lower their capacity. Examples of such bronchial disorders are inflammation in the airways, training-induced lung haemorrhage and allergy.

In particular allergic bronchial disorders are a great and steadily increasing problem with sports horses, trotting horses, and racehorses.

It is known to prevent and/or treat allergic bronchial disorders in horses by inhalation therapy, which is a method of treatment whereby the horse is caused to inhale a microparticular therapeutic agent, such as a steroid or a beta-2-agonist, e.g. in the form of an aerosol. Various inhalation devices have been developed for this purpose.

A known commercial inhalation device consists of three parts, viz. an electronically operated compressor for generating an atomizing pressure, a mask with a built-in atomizing chamber, and one or more drug atomizers connected with the compressor and being positioned within the atomizing chamber, by means of which atomizers a cloud of micro-particles of the therapeutic agent used can be formed in the atomizing chamber.

The mask used is intended for positioning over the horse's muzzle which, just like the noise from the compressor, tends to make the horse uneasy. Further, the use of the know device presupposes the availability of an electric supply source at the site of treatment. These circumstances cause the treatment to be cumbersome, i.e., also because the atomization of the drug takes about 10 minutes and requires that the horse is tied up in order to make it stand still during the treatment.

Devices are also known which are based on use of manually operated drug atomizers, e.g. in the form of an aerosol container provided with a manually operated valve, which when operated manually causes a cloud of micro-particles to be formed in a mask positioned on the horse's muzzle, also shaped as a nosebag and covering both nostrils. Such a device may comprise an inhalation spacer in which the atomization of the drug takes place, and from which the horse via the mask breathes in the treatment agent. As mentioned above, the use of a mask for positioning over the horse's muzzle may cause problems, in particular when treating uneasy horses.

It is also known to treat allergic bronchial disorders by manually closing one of the horse's nostrils and positioning a supply pipe in the other nostril, and by directly atomizing the treatment agent into the supply pipe.

When using such a device it is a risk that the atomization of the drug does not take place synchroneously with the horse's breathing in, and that the micro-particles are deposited on the mucosa in the nasal cavity, and consequently do not get to the bronchi or the lungs. Also, the device requires that the treatment is performed by a veterinary.

It is the object of the present invention to provide a treatment device the operation of which is so uncomplicated that a treatment of the horse can be performed without the assistance of a veterinary, the use of which does not make the horse uneasy, and which provides great security that the treatment agent reaches the places in the airway system which it is desired to treat.

The device according to the invention comprises an inhalation spacer with a first and a second opening, an activatable drug atomizer which can be connected with the first opening in the inhalation spacer, and connecting means for connecting the second opening of the inhalation spacer with the airways of a horse and with a valve arrangement comprising two oppositely acting one-way valves, one one-way valve of which allows influx of inhalation air from the interior of the inhalation spacer to the connection means, and the other one-way valve allows outflux of exhalation air from the connecting means to the ambient air, and is characterized in that the connecting means comprises a hopper-shaped part, which at the hopper opening has such size that is able to cover only one of the horse's nostrils, and which at the opposite end is connected with the inhalation spacer via the valve arrangement, and that the inhalation spacer has at least one third opening with a co-operating one-way valve which permits influx of air from the surroundings into the interior of the inhalation spacer.

The treatment of a horse with the device according to the invention may be effected by positioning the hopper-shaped part over one of the horse's nostrils while maintaining the other nostril open or by closing it manually.

Either immediately before or simultaneously with or immediately after the hopper-shaped part is positioned over one of the horse's nostrils, an activation of the drug atomizer is performed so that a cloud of micro-particles of the treatment agent is generated in the inhalation spacer. When the horse inhales, an underpressure will arise in the inhalation spacer, which entails that air will flow into the inhalation spacer from the surroundings through the third opening, and the air flow will pass through one of the one-way valves (the inhalation valve) of the valve arrangement into the hopper-shaped, and further on into the horse's airways. This air flow will entrain the micro-particles floating in the inhalation spacer, and thus carry the treatment agent into the airways. When the horse exhales, the exhalation air will pass out of the device through the second one-way valve (the exhalation valve) of the valve arrangement.

As will appear from the above, the device according to the invention is uncomplicated and easily operated. Since it furthermore only requires that the hopper-shaped part of the device is positioned in slight contact with the area around one of the horse's nostrils and is not noisy, it will not scare the horse. At the same time, the treatment time can be reduced e.g. to less than 1 min.

These factors entail that the treatment of the horse can be performed by persons without veterinary background.

The device according to the invention offers the additional advantage that large amount of air will flow through the inhalation spacer. Thus, each time the horse inhales, an amount of air of about 10 liters will be passed through the inhalation spacer. If the spacer e.g. has a volume of about 1 liter, which makes it easy to handle, by and large the entire amount of treatment agent which has been introduced into the inhaler spacer will be entrained by the inhalation air and carried down into the horses' airways. Thus, the device ensures good utilization of the amount of treatment agent used, and restricts the settlement of drug at unintended sites in the airways.

The activatable drug atomizer appertaining to the device according to the invention preferably comprises an aerosol container, i.e. a container containing a pressurized gas and solid drug particles. However, use can also be made of a mechanical atomizer, just as the drug may be present in the liquid phase.

The inhalation spacer preferably has an outer shape like a solid of rotation, and may e.g. be made of metal or plastic. The latter is preferred for reasons of weight.

The hopper-shaped part preferably comprises a pipe socket which is adapted to be placed around a similar pipe socket provided around the second opening of the inhalation spacer, the latter pipe socket having oppositely placed axially extending incisions which when the two parts are assembled are covered by flexible flaps provided at each side of the pipe socket of the hopper-shaped part, and which have such a flexibility that they open outwardly during exhalation of air and are prevented from moving inwardly during inhalation.

In this embodiment another one-way valve is provided in the second opening of the spacer.

The connecting means may also comprise two parts, viz. a pipe socket and a hopper-shaped part. The former, which preferably comprises two ducts, a one-way valve being positioned in each duct, is preferably made of transparent plastic, whereby it is made possible to control that the one-way valves in use act as intended.

The free end of the hopper-shaped part, which is intended to cover one of the horse's nostrils, is preferably made of flexible plastic, so that by contact with that part of the horse's muzzle which surrounds the nostrils, it conforms to the muzzle without annoying the horse.

Figure 2:
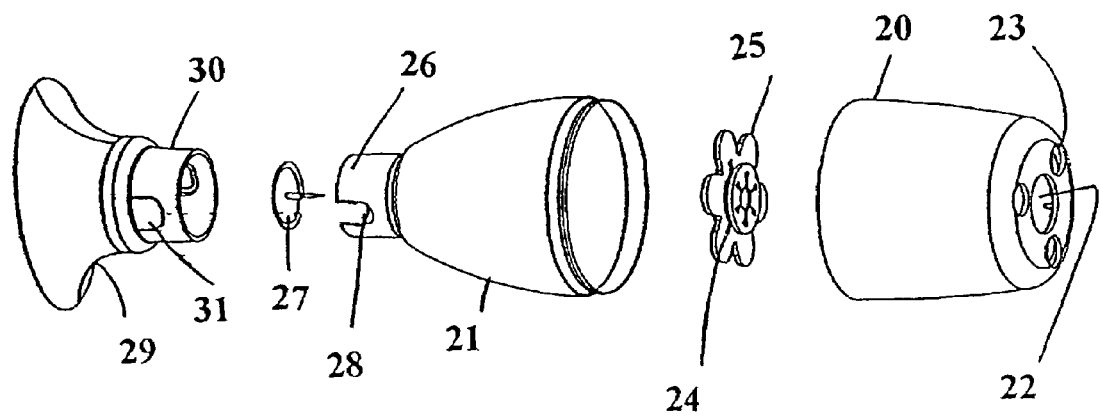
Figure 3:

In the following the invention is described in more detail with reference to the drawings, in which FIG. 1 shows a longitudinal section through a preferred embodiment of a device according to the invention, FIG. 2 shows an exploded view of another preferred embodiment of a device according to the invention, and FIG. 3 shows a device according to the invention in operating position.

In the drawing 1 is an inhalation spacer composed of two parts 2 and 3, which together delimit an atomizing chamber 4. The spacer part 2 has at its free end a central opening 5 having such shape that when introducing a dispenser part 6 of an activatable drug atomizer 7, an air-tight connection is formed between the drug dispenser 7 and the spacer part 2. In the area around the central opening two or more additional openings 8 are provided, each of which is provided with a one-way valve in the form of a flap valve 9 which allows influx of air from the surroundings into the atomizing chamber 4 when a sub-atmospheric pressure arises therein.

At its free end the spacer part 3 has an opening 10 into which one end of pipe socket 11 has been inserted air-sealingly, which socket comprises two ducts 12 and 13 and at its opposite end has been fitted with a hopper-shaped part 14 being flexible at its free end 15 and having such size as to be able to cover one of a horse's nostrils.

A one-way valve in the form of a flap valve is built into the duct 12, which valve allows air to flow from the atomizing chamber 4 into the interior of the hopper-shaped part 14, and prevents air from flowing in the opposite direction. The duct 13 is closed at the end facing the atomizing chamber 4, and is provided with a branch pipe 17 into which a one-way valve in the form of a flap valve 18 has been inserted, which valve allows outflux of air from the interior of the hopper-shaped part 14 to the surroundings and prevents air flow in the opposite direction.

When using the device shown, the free end 15 of the hopper-shaped part 14 is positioned over one of a horse's nostrils, and the other nostril is closed manually. Then the drug atomizer 7 is activated, whereby a cloud of drug particles is formed in the atomizing chamber 4. When the horse inhales, a sub-atmospheric pressure will arise in the atomizing chamber 4, which will entail that air flows into the atomizing chamber 4 through the openings 8, and further on through the duct 12 in the pipe socket 11, the hopper-shaped part 14, the horse's nostril, and further on into its airways. The air flow thus formed will cause the drug particles present in the atomizing chamber 4 to be entrained and passed into the horse's airways.

During the horse's exhalation, the exhalation air passes out through the duct 13 and the branch pipe 17 to the surroundings. After a few inhalation, by and large all drug particles in the atomizing chamber will have been removed herefrom and have been introduced into the horse's airways.

When cleaning the device, the dispenser part 6 of the drug atomizer is removed through the central opening 5, and the pipe socket 11 with affixed hopper-shaped part 14 through the opening 10 in the spacer part 3. The spacer 1 can then be disassembled into the two spacer parts 2 and 3.

Having thus been disassembled, the device can easily be cleaned and made ready for renewed use.

The device shown in FIG. 2 comprises a spacer consisting of two parts 20 and 21. In the end of the first part 20, there is provided an opening 22 for insertion of an activatable drug atomizer and a one-way valve arrangement comprising openings 23 and a valve member 24 having flexible valve flaps 25 covering the openings 23.

The second part 21 of the spacer comprises a pipe socket 26 surrounding a valve comprising a valve member 27.

Two opposite axially extending incisions 28 are provided in the pipe socket 26.

The spacer also comprises a hopper-shaped part 29 comprising a pipe socket 30 comprising two flexible valve flaps 31 which when the pipe socket 30 is placed around the pipe socket 26 overlap the incisions 28 in such a manner that the flaps 31 can move outwardly and are prevented from moving inwardly. Thus, this arrangement functions as a one-way valve allowing exhalation air from passing out from the hopper-shaped part and preventing the influx of air during inhalation.

FIG. 3 illustrates the way in which a device according to the invention is to be used.

The invention claimed is:

1. A method of treating a bronchial disorder in a horse, the method comprising:

(a) providing an inhalation device, the device comprising a hopper-shaped part having a radially symmetric outer surface operably connected to a tapered inhalation spacer and a drug atomizer, the hopper-shaped part constructed to cover only one of the horse's nostrils;

(b) placing the hopper-shaped part over only one nostril of the horse;

(c) closing the horse's other nostril; and (d) after placing the hopper-shaped part over only the one nostril, treating the horse.

2. The method according to claim 1, wherein treating the horse comprises:

(a) passing about 10 liters of air through the inhalation spacer.

3. The method according to claim 1, wherein treating the horse comprises:

(a) passing up to about 10 liters of air through the inhalation spacer.

4. The method according to claim 1, wherein treating the horse comprises:

(a) treating the horse for less than 1 minute.

* * * * *